(12) United States Patent
Rogers et al.

(10) Patent No.: US 9,241,482 B2
(45) Date of Patent: *Jan. 26, 2016

(54) SELF-DECONTAMINATING SURFACE COATINGS AND ARTICLES PREPARED THEREFROM

(75) Inventors: Martin E. Rogers, Blacksburg, VA (US); Janice P. Phillips, Hattiesburg, MS (US); Bryan Koene, Blacksburg, VA (US); Marc S. Hirsch, Roanoke, VA (US); James H. Wynne, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1414 days.

This patent is subject to a terminal disclaimer.

(21) Appl. No.: 11/548,406

(22) Filed: Oct. 11, 2006

(65) Prior Publication Data

US 2008/0050410 A1    Feb. 28, 2008

Related U.S. Application Data

(60) Provisional application No. 60/725,341, filed on Oct. 11, 2005.

(51) Int. Cl.
| | |
|---|---|
| *A01N 25/34* | (2006.01) |
| *A01N 33/12* | (2006.01) |
| *A01P 1/00* | (2006.01) |
| *A01N 25/10* | (2006.01) |
| *C09D 5/14* | (2006.01) |

(52) U.S. Cl.
CPC ............... *A01N 25/34* (2013.01); *A01N 25/10* (2013.01); *A01N 33/12* (2013.01); *C09D 5/14* (2013.01)

(58) Field of Classification Search
None
See application file for complete search history.

(56) References Cited

U.S. PATENT DOCUMENTS

| | | | | |
|---|---|---|---|---|
| 4,539,363 | A | * | 9/1985 | Backhouse ................... 524/460 |
| 4,844,983 | A | | 7/1989 | Parker |
| 5,428,123 | A | * | 6/1995 | Ward et al. ....................... 528/28 |
| 6,235,351 | B1 | | 5/2001 | DiMarzio et al. |
| 6,569,353 | B1 | | 5/2003 | Giletto et al. |
| 6,656,919 | B1 | * | 12/2003 | Baugh et al. .................... 514/46 |
| 6,699,433 | B2 | | 3/2004 | Weinberg et al. |

(Continued)

FOREIGN PATENT DOCUMENTS

| | | | |
|---|---|---|---|
| DE | 10043710 A | * | 3/2002 |
| WO | WO 0166471 A2 | * | 9/2001 |
| WO | WO 2004090064 A1 | * | 10/2004 |

OTHER PUBLICATIONS

U.S. Appl. No. 11/183,305, Wynne et al.

(Continued)

*Primary Examiner* — Bethany Barham
*Assistant Examiner* — Dominic Lazaro
(74) *Attorney, Agent, or Firm* — US Naval Research Laboratory; Joseph T. Grunkemeyer (57) ABSTRACT

The present invention is directed toward a self-decontaminating surface coating, which when cured has a partially hydrophobic surface. The coating comprises a polymeric coating resin which, when cured, is hydrophilic. The coating also comprises a biocide, a germinating agent, and a hydrophobic micro/nano particulate material. The coating is suitable for application to ceramics, metals, and polymer substrates. Articles coated with the coating of the present invention are resistant to spores.

21 Claims, 3 Drawing Sheets

(56) References Cited

U.S. PATENT DOCUMENTS

| | | |
|---|---|---|
| 2002/0086044 A1* | 7/2002 | Voris et al. .................... 424/406 |
| 2002/0107495 A1* | 8/2002 | Chen et al. .................... 604/365 |
| 2003/0175318 A1* | 9/2003 | Schilling et al. ............. 424/405 |
| 2005/0191206 A1 | 9/2005 | Buhr et al. |
| 2006/0073067 A1 | 4/2006 | Schilling et al. |
| 2008/0021131 A1* | 1/2008 | Mertens et al. ............... 523/111 |

OTHER PUBLICATIONS

Search Report and Written Opinion in PCT/US06/39676 (Aug. 20, 2007).

\* cited by examiner

SELF-DECONTAMINATING SURFACE COATINGS AND ARTICLES PREPARED THEREFROM

CROSS-REFERENCE TO RELATED APPLICATIONS

This application claims the benefit of U.S. Provisional Patent Application Ser. No. 60/725,341, entitled, "Self-Decontaminating Surface Coatings and Articles Prepared Therefrom," filed Oct. 11, 2005, which is hereby incorporated by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W911NF-04-C-0084 awarded by DARPA/US Army Research Office.

FIELD OF THE INVENTION

The present invention is related to coatings. In particular, the invention is related to coatings that make a surface self-decontaminating.

BACKGROUND OF THE INVENTION

Spores are known to form from aerobic Bacilli, anaerobic Clostridia, selected sarcinae and few actinomycetes. Spores resemble certain plant seeds in that they do not carry out any metabolic reactions. In this regard, they are especially suited to withstand severe environmental stress and are known to survive prolonged exposures to heat, drying, radiation and toxic chemicals. These properties make spores especially difficult to kill in environments, like living tissue or objects which come in contact with living tissue, which would be adversely effected by extreme conditions.

Pathogenic spore-forming bacterial like *Bacillus anthracis, Clostridium botulinum, C difficile, C. perfringens* and *C. tetani* form spores which survive in harsh environmental conditions for extended periods. The spore nucleoid structure is surrounded by protective layers composed of peptidoglycan and proteins with unusual amino acid contents. This structure provides unique resistance properties acting as a permeability barrier to prevent access to the underlying spore protoplast. Spores are able to survive exposure to chlorinated solvents, detergents, mechanical disruption, extreme temperatures, UV and ionizing radiation. Hence, there is a need to develop a means to prevent the spread of spores once they have contacted a surface.

Most conventional liquid sporicidal agents fall into three broad categories: halide releasing compounds (hypochlorites and idodophores), reactive oxygen releasing agents (peroxides and peracetic acid) or aldehydes (formaline and glutaraldehyde). Activity of all of these agents depends on destruction of fundamental metabolic processes and organic structures making them extremely hazardous to humans. Furthermore, many of these agents rely on the generation of very reactive chemical species, making them inherently unstable. Most commercial sterilants require activation immediately prior to use and loose effectiveness within hours after application. The efficacy of some agents such as hypochlorites is rapidly attenuated by the presence of organic matter. Aldehydes are effective sporicides only at relatively high concentrations (2-10%) as liquids and require high relative humidity for effectiveness as a vapor. Building decontamination has utilized extremely toxic gases such as ethylene oxide, chlorine dioxide and methylene bromide. As with the aldehydes, sporicidal efficacy of these gasses requires high relative humidity and extreme caution must be exercised during use. The ability to determine the successful removal of spores from a surface using one of the aforementioned processes is difficult.

One method for decontaminating biological spore contamination has involved the use of a spore germination composition, over a sufficient time period, to cause germination of the biological spores. With the spores germinated within a contaminated area, select disinfectants show increased effectiveness against the spores. Upon germinating, the spore cortex breaks down, losing heat and chemical resistance, which results in increased susceptibility to being killed by the decontaminant. This method fails to eliminate the problem of successfully removing spores from the surface. Rather, it requires the spores to become part of the surface and to undergo germination prior to removal.

Giletto et al. in U.S. Pat. No. 6,569,353 describe a formulation for decontamination which includes a sorbent material or gel, a peroxide source, a peroxide activator, and a compound containing a mixture of $KHSO_3$, $KHSO_4$, and $K_2SO_4$. The formulation is self-decontaminating and once dried can easily be wiped from the surface being decontaminated. This formulation, although useful for an already decontaminated surface, is ineffective as a preventative means for keeping a surface free of contamination.

DiMarzio et al. in U.S. Pat. No. 6,235,351 propose a method for producing a self-decontaminating surface. The method includes exposing a surface to be treated to ultraviolet light and then applying a coating of nanoparticles of a transition metal oxide to the surface. The nanoparticles are heated to 750° C. and sprayed onto the surface to form a nanoparticle coating. The treated surface is exposed to ultraviolet light and water moisture to catalytically form free hydroxyl radicals that thereafter react with contaminants to render them generally harmless. Such a method is cumbersome and not feasible for surfaces that cannot withstand having 750° C. nanoparticles applied thereon.

Buhr et al. in U.S. Patent Application Publication 2005/0191206A1 describe a decontaminating method for biological spore populations which uses the application of an acidic environment to the biological spores with an additional step of moderately heating the biological spores in the acidic environment to decontaminate the spores. As in other methods, this method is only useful for treating surfaces after exposure to biological spores and is not suitable as a preventative measure against spores.

An object of the present invention is to provide a self-decontaminating surface coating or treatment process which, when applied to an article, makes the coated surface of the article hostile towards spores.

Another object of the present invention is to provide a self-decontaminating surface coating or treatment process that facilitates easy removal of spore clusters and elimination of any spore fragments that may penetrate the surface of the coating.

Another object of the present invention is to provide a method for preparing an article that is resistant to spores.

SUMMARY OF THE INVENTION

The present invention is directed toward a self-decontaminating surface coating, which, when cured, has a partially hydrophobic surface. The coating comprises a polymeric coating resin which, when cured, is hydrophilic. The coating also comprises a biocide, a germinating agent and a hydrophobic micro/nano particulate material. When the coating is cured, it has a partially hydrophobic three-dimensional surface and is resistant to spore growth. The coating is suitable for application to ceramics, metals, and polymer substrates. Articles coated with the coatings of the present invention have surfaces that are self-cleaning, creating a hostile environment for spores.

Additional objects and advantages of the invention will be set forth in part in the description which follows, and in part, will be obvious from the description, or may be learned by practice of the invention.

BRIEF DESCRIPTION OF THE DRAWINGS

The accompanying drawing illustrates a complete embodiment of the invention according to the best modes so far devised for the practical application of the principals thereof, and in which.

DETAILED DESCRIPTION OF THE PREFERRED EMBODIMENTS

The self-decontaminating surface coating of the present invention, when applied to the surface of an article, makes the article hostile towards spores and easy to clean. These coatings have many applications where a preventative measure is desirable to discourage, control or eliminate the damage caused by spores. For example, the coatings of the present invention are applicable in hospital settings where it is desirable to control or minimize nosocomial infections caused by bacterial spores. In particular, antibiotic-associated infections such as *Pseudomembranous colitis*, the lethal form of diarrhea commonly caused by hospital-acquired *Clostridium difficile* colonization of the large bowel, is minimized when surfaces such as countertops are kept clean and free from bacterial spores. In addition, the coatings of the present invention are useful in the building industry for controlling "sick building syndrome" often caused by growth and accumulation of highly allergenic sporulating fungi within walls and concealed places, such as duct work, where high humidity or moisture build-up occurs.

The self-decontaminating surface coating of the present invention comprises a polymeric coating resin which, when cured, is hydrophilic. The coating further comprises a biocide, a germinating agent, and hydrophobic micro/nano particulates. As an alternative embodiment, the coating also contains superabsorbent polymer particulate. When the coating is cured, it has a partially hydrophobic surface which is three-dimensional, creating a surface that is hostile towards the accumulation of spore clusters and spore growth.

Figure 1:
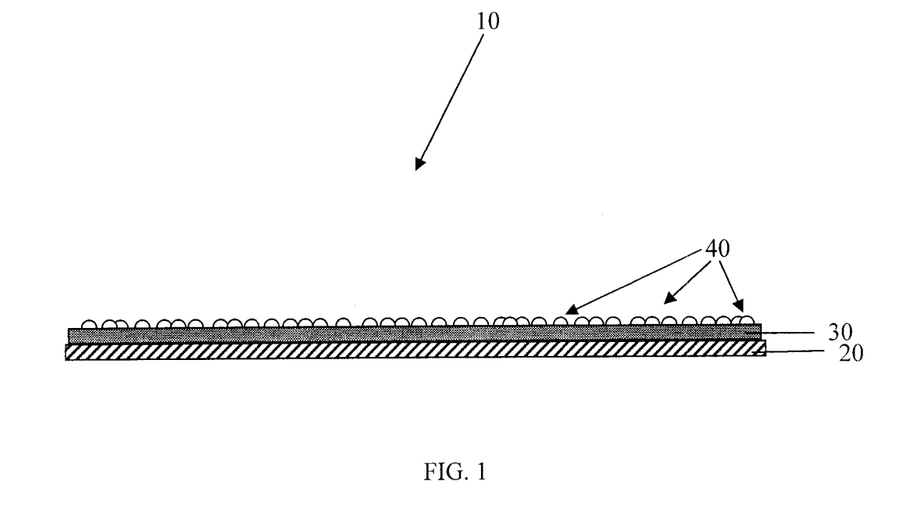
FIG. 1 depicts a surface having the self-decontaminating coating applied thereon.

The self-decontaminating surface is achieved by a two-fold mechanism. First, the surface of the cured coating is partially hydrophobic. The partially hydrophobic surface, which is comprised of three-dimensional hydrophobic micro/nanoparticles that protrude from the surface of the coating, facilitates the removal of spores by allowing spore clusters to be easily washed off from the surface of an article that is coated with the coating. Next, in the event individual spores are able to penetrate between the hydrophobic mico/nano particulates found on the surface of the coating, the coating contains a hydrophilic resin that, when coupled with a germinating agent, encourages spore growth into a vegetative state. Once the spore has reached its vegetative state, a biocide in the coating is able to kill the cell, rendering the spore harmless.

The polymeric coating resin employed in the present invention is any polymeric coating resin that, when cured, is hydrophilic. Ideally, the resin system allows transport of water, nutrients, and germinants, accommodates biocidal activity, and is compatible with the hydrophobic micro/nano particles that are incorporated into the coating. The polymer is also flexible, tough, and has excellent adhesive properties. In a preferred embodiment of the invention, the cured polymeric coating resin has an equilibrium water uptake ranging from about 5% by weight to about 75% by weight of the cured resin. In a most preferred embodiment of the present invention, the cured polymeric coating resin has an equilibrium water uptake of about 20% by weight of the cured resin. The hydrophilicity of the resin enables the coating to absorb any water vapor that may penetrate into the coating. This water may serve as an eventual source of moisture to encourage spore germination into the vegetative state. Particular polymeric coating resins that are suitable for the present invention include but are not limited to polyurethane, epoxy, acrylic, acrylic monomers, vinyl acrylic, vinyl ester, ethylene vinyl acetate and combinations thereof as both one and two-part systems. In a most preferred embodiment of the invention, the polymeric coating resin is a two-part, cationic water dispersed polyurethane and hydrophilic IPDI prepolymer, an example of which known as WITCO™ 213 which is commercially available from Crompton Chemical, and HYPOL™ G-50, which is commercially available from the Dow Chemical Company.

A biocide is combined with the polymeric coating resin for the purpose of killing microbial pathogens. In particular, the biocide is capable of acting on spores which have undergone germination to the vegetative state. Preferred biocides of the present invention include but are not limited to: phenols; substituted phenols; hypochlorites (chlorine-releasing agents); formaldehydes (formaldehyde-releasing agents); gluteraldehydes; mecurials; quaternary ammonium compounds; pyridinium compounds; aliphatic alcohols; amines; sulfates; carboxylic acids; ethanols; piperidine-N-oxide; chlorohexidines; azideisothiazolones; iodoacetates; heavy metal salts (silver, copper, mercury); chloroacetamides; oxines; hydrogen peroxide (peroxide releasing agents); peracetic acids; aminoacrilines; and chlorophenols. Particular examples of biocides include but are not limited and TRICLOSAN™ which is commercially available from Unicho. Alternatively, biocides that have been engineered to have certain surface active properties may also be employed. The biocide is added to the coating formation at an amount sufficient to kill any germinated spores. In particular, the amount of biocide ranges from about 0.05% by weight to about 5% by weight of the cured coating, and, preferably, 0.1 to 1.5% by weight of the cured coating.

In order to convert a bacterium from the spore state into a vegetative state, a germinating agent is included in the coating formulation. The germinating agent facilitates spore conversion on the hydrophilic polymer. Any germinating agent may be used in the present invention and, in particular, the germinating agent is L-alanine, L-methionine, and combinations thereof. The germinating agent is added to the coating at an amount ranging from about 0.1% by weight to about 5% by weight of the cured coating. Most preferably, the germinating agent is added at about 1% by weight of the cured coating.

In an alternate embodiment of the invention, a nutrient is added to the coating. The nutrient is generally present to enhance development of the bacteria from the spore to the vegetative state. Suitable nutrients include, but are not limited to: Luria broth; yeast extract;

and combinations thereof. The nutrient is present at an amount sufficient to encourage growth. In particular, the nutrient comprises up to about 5% by weight of the cured coating. More particularly, the nutrient comprises about 1% by weight of the cured coating.

As an alternative embodiment of the invention, a superabsorbant polymer is added to the coating formulation to serve as a source of hydration during the germination of the spores. Superabsorbant polymers have the ability to absorb many times their weight in water. Any superabsorbant polymer known to one of ordinary skill in the art may be employed in the present invention such as those known and described in U.S. Pat. Nos. 5,461,085; 5,525,703; 5,612,384 and 5,669,894 the disclosures of which are hereby incorporated by reference in their entirety. Superabsorbant polymers are commercially available in a variety of chemical forms, including substituted and unsubstituted natural and synthetic polymers, such as hydrolysis products of starch acrylonitrile graft polymers, carboxymethylcellulose, crosslinked polyacrylates; sulfonated polystyrenes; hydrolyzed polyacrylamides; polyvinyl alcohols; polyethylene oxides; polyvinylpyrrolidones; and polyacrylonitriles. The superabsorbant polymers are preferably used in the form of a particulate. By "particulate" it is meant to include granules, fibers, flakes, spheres, powders, platelets, and other forms known to those of ordinary skill in the art. Superabsorbing polymer particles have a nominal particle size (i.e., the size of a particle capable of passing through a screen of predetermined mesh size) of less than about 1 micron to up to about 200 microns. Preferably, the superabsorbant polymer is in the form of a particulate having a mesh size ranging from about 5 to about 50 microns.

Hydrophobic micro/nano particulates are added to the formulation to impart a superhydrophobic property to the cured coating surface. Hydrophobic micro/nano particulates are particles (preferably silica microspheres) having dimensions of less than 100 micrometers and less than 100 nanometers. The addition of these particulates to the coating composition causes the cured surface of the coating to have an advancing water contact angle greater than about 150 degrees and a receding water contact angle greater than about 150 degrees. Rough surfaces with low surface energy have the ability to attain very high contact angles and, therefore, are considered to be ultrahydrophobic. Microscopically, these surface structures require a combination of roughness on a microscale (1-50 μm) as well as on a nanoscale (1-50 nm). The particulates can be added to the formulation either by direct mixing, addition to the surface of the coating once it has achieved a tacky state to touch, or a combination of the two. When particulates are added directly to the coating formulation, the particle size must be large enough to protrude from the surface of the coating when the coating is applied to and cured on a substrate or article. In one embodiment, the micro/nano particles are used to coat super-absorbing polymer microspheres. Alternatively, the micro/nano particles are treated with a hydrophobic surface treatment such as a fluorosilane, alkyl silane, silicone, or other hydrophobic surface treatments known to those of ordinary skill in the art.

When superabsorbant polymer particulates are added to the coating composition of the present invention, the nutrients and germinants are either incorporated into the coating at the same time or the nutrients and germinants are dissolved in water, combined with the superabsorbant polymer particulates to form a mixture, wherein the mixture is subsequently added to the coating composition.

The coating formulation presented herein is not limited to the components described herein. Fillers, stabilizers, antioxidants, and pigments may also be added to the coating system. The addition and amounts of these materials is based on the knowledge of one of ordinary skill in the art who is engineering the coating to meet the requirements of the particular application.

FIG. 1 depicts a cross-sectional view of the self-decontaminating surface coating 10 of the present invention as it is applied to an article 20. Adhesion to the surface of an article is achieved by way of the hydrophilic polymeric coating resin 30. This resin also serves as a carrier medium for the added components of the system. Contained within the coating are a biocide (not shown), a germinating agent (not shown), and a hydrophobic micro/nano particulate 40. One will note that the micro/nano particulate protrudes from the surface of the rest of the coating.

In preparing articles of the present invention, an article is provided and the self-decontaminating surface coating of the present invention is applied and subsequently cured thereon. Various articles of the present invention include but are not limited to: children's toys and public play equipment, hospital surfaces, door knobs, public transportation surfaces, fabric/clothing, food preparation surfaces, air handling ducts, duct work, countertops, walls, particularly in medical facilities, vertical interior walls (back studs), cutting surfaces, food handling and packaging plants, military equipment and shelters, and military vehicles and vessels. When applying the coating, it is desirable to apply the coating at a thickness wherein the micro/nano particulate protrudes from the surface of the coating to impart sufficient hydrophobicity to the surface of the article. As an alternative embodiment of the method of the present invention, the self-decontaminating surface coating is cured to have a tacky surface to touch and the hydrophobic micro/nano particulates are applied to the tacky surface by sprinkling the hydrophobic micro/nano particulates on the tacky surface. The articles prepared by the method of the present invention comprise a three-dimensional surface coating and have a surface which is hostile to spores and spore growth.

EXAMPLES

Example 1

Preparation of Biocide: N-9045-72

(Hexadecyl-(2-methoxy-ethyl)-dimethyl-ammonium bromide)

In a 20 mL round bottomed flask equipped with reflux condenser and a positive flow of nitrogen were placed a tertiary amine (Hexadecyl-dimethyl-amine) (6.36 mmol), a bromo-ethyleneglycol monomethyl ether (1-Bromo-2-methoxy-ethane) (6.36 mmol), and absolute ethanol (17.49 mmol). The solution was heated in an 83° C. oil bath for 24 hr. The resulting solution was allowed to slowly cool to rt and concentrated under reduced pressure. The resulting thick yellow oil was titrated with petroleum ether (2×3 mL), and placed under vacuum to remove trace solvent. The resulting product was dissolved in 2 mL of EtOH with vigorous stirring and then cooled to −30° C. to result in crystallization of the desired product (Hexadecyl-(2-methoxy-ethyl)-dimethyl-ammonium bromide). A second crop of equal purity may be recovered by recrystallization of the mother liquor.

Example 2

Preparation of the Self-Decontaminating Surface Coating 3.6 grams of HYPOL™ G-50 (a isocyanate functional polyethylene glycol polymer, serving as a hydrophilic coating component, commercially available from Dow Chemical Corporation) was dissolved in 18 grams of acetone with stirring. 76.3 mg of N-9045-72 was dissolved in 10 grams of deionized water to which 13.3 grams of Witco-213 (a cationic polyurethane dispersion in water commercially available from Crompton Chemical) was added in a Flaktek cup. 382 mg of polyacrylamide microspheres (a superabsorbent polymer) that had been soaked in nutrient broth was then added to the solution. The nutrient broth was prepared by dissolving 4 grams of yeast extract, 2 grams of L-alanine and 2 grams of L-methionine in 32 grams of deionized water. This solution was then filter sterilized. Two grams of polyacrylamide microspheres were then added to 2 grams of the nutrient broth solution, and they were allowed to soak up the solution for approximately two hours before use. The Hypol/acetone solution was then added to the cup. The sample was mixed in the speed mixer at 2000 rpm for 2 minutes. The sample was then pipetted onto glass slides and allowed to dry approximately 20 to 30 minutes until tacky. After the sample had become tacky, silica (Silica Gel from Selecto Scientific (32-63 microns)) was sprinkled onto the top of the coating and removed by shaking off the excess. The samples were allowed to dry overnight at room temperature. The next morning fluorosilane was applied to the coating with a sponge brush. The sample was allowed to dry at room temperature and then placed in the oven overnight at 80° C. The coating without biocide contains 7.63 grams of solid (17% solids). The coating was challenged with $10^7$ CFU/ml of *Staphylocuccus aureus*. After two hours exposure, the coating induced a seven log kill of the bacteria. The contact angle of the coated slide was measured at 143°. Results have shown that the self-decontaminating coating when challenged with $10^7$ CFU/ml *B. anthracis* (Sterne) spores effects a 4 log kill of the spores.

Example 3

Testing of Surface Active Biocides

Coating Additives:
1. Biocidal Additive A:

2. Spore Germination Additive B:

The nutrient broth is made by adding 4 grams of yeast extract, 2 grams of L-alanine, 2 grams of L-methionine and 32 grams of deionized water to a 100-mL glass beaker. The mixture is then placed on a hot plate with stirring and minimal heat to give the nutrient broth solution.

3. Superabsorbent Polymer (SAP) Additive C:

2 grams of superabsorbent polyacrylamide polymer microspheres were added to 2 grams of spore germination Additive B. The microspheres were then allowed to absorb the nutrients for a 1 hour period.

Coating Formulation:

3.6 grams of HYPOL™ G-50 (The Dow Chemical Company) IPDI prepolymer was dissolved in 18 grams of acetone with stirring. In order to ensure complete dissolution of the prepolymer into acetone the sample was left stirring at room temperature for 30 minutes. The sample was also covered with Parafilm to prevent loss of acetone during the dissolution process. 76.3 mg of Biocidal Additive A was dissolved in 9 grams of dl water to which 1 gram of Spore Germination Additive B was added. This solution was then added to 13.3 grams of Crompton Corporations WITCOBOND™-213 cationic polyurethane dispersion. 382 mg of Superabsorbent Polymer (SAP) Additive C was then added to the solution resulting in the water based component of this coating formulation. The Hypol/acetone prepolymer solution was then added to the water containing component of the formulation. The sample was then mixed in a high speed orbital mixer at 2000 rpm for 2 minutes resulting in the desired two component resin system consisting of the needed biocidal, water delivery and germinant moieties. The final solid loading of the additives is as follows: 1% Biocidal Additive A, 13% Spore Germination Additive B and 5% Superabsorbent Polymer Additive C.

Coating Application:

The sample formulated as described above was then pipetted onto 1"×3" cleaned glass slides and allowed to dry approximately 20 to 30 minutes until tacky. After the sample had become tacky silica gel was then sprinkled onto the top of the coating. The samples were allowed to then completely cure overnight at room temperature. The excess silica not bound to the surface of the film was removed by gentle shaking of the slides. The next morning a fluorosilane solution then was applied to the coating with a sponge brush. The sample was allowed to dry at room temperature and then placed in the oven overnight at 80° C. to ensure complete fluorosilane reaction to the silica.

Results:

The three selected surface active biocides were found to be effective against a variety of bacteria. Table 1 represents the results of the testing. A polyurethane coating without any biocide added (control) exhibited some antimicrobial activity. All three surface active biocides exhibit antimicrobial activity above that of the control sample. All three surface active biocides are highly effective against Gram-positive (*B. anthraces* (Sterne)) and Gram-negative (*E. Coli*) bacteria. The effectiveness of these quaternary ammonium surface active biocides against Gram-negative bacteria is unexpected.

TABLE 1

| Compound | Average log kill B. anthraces (Sterne) |
|---|---|
| Control | 1 ± 1 |
| [structure: C15 alkyl quaternary ammonium with Br⁻, N⁺ with methyl, ethoxy-methyl group] | 5 ± 1 |
| [structure: C7 alkyl quaternary ammonium with Br⁻, N⁺ with methyl, ethoxy-methyl group] | 3 ± 1 |
| [structure: C7 alkyl quaternary ammonium with Br⁻, N⁺ with methyl, longer ethoxy-ethoxy-methyl group] | 3 ± 1 |

Example 4

10× Challenge of *Bacillus anthracis* (Sterne)

Self-decontaminating surface (SDS) demonstration coatings were prepared for the 10× challenge against *Staphylococcus aureus*. The purpose of the 10× challenge is to demonstrate the durability of the SDS coating over multiple exposures to spores.

Coatings were prepared from the aqueous based two part urethane (some acetone added) containing the nutrients/germinants, SAP microspheres and a biocide. The resin was applied to 1"×3" glass slides. To achieve a superhydrophobic surface, silica was applied as the coating become tacky followed by treatment with a fluorosilane.

*Bacillus anthracis* (Sterne) is applied to the slides by aerosolizing from a solution of $10^9$. This is done in a special hood with filters to collect any of the bacteria that may escape. The solution is sprayed at a slight angle but not 45° to avoid beading and rolling off the surface. To insure application of $10^7/cm^2$, a blank glass slide is sprayed and swabbed followed by serial dilution. After spraying, the slides are placed in a petri dish with sterile damp filter paper to prevent to dessication for two hours before additional challenge trials. At each challenge, slides are removed and a one $cm^2$ swabbed for serial dilution.

The data obtained from the 10× challenge is given in Table 2. The data is depicted graphically in FIG. 2. The data from each challenge is an average of three samples. The data is depicted in the graph as Mean Diamonds. The line across each diamond represents the group mean. The vertical span of each diamond represents the 95% confidence interval for each group. For groups with equal sample sizes, overlapping marks indicate that the two group means are not significantly different at the 95% confidence level.

Figure 2:
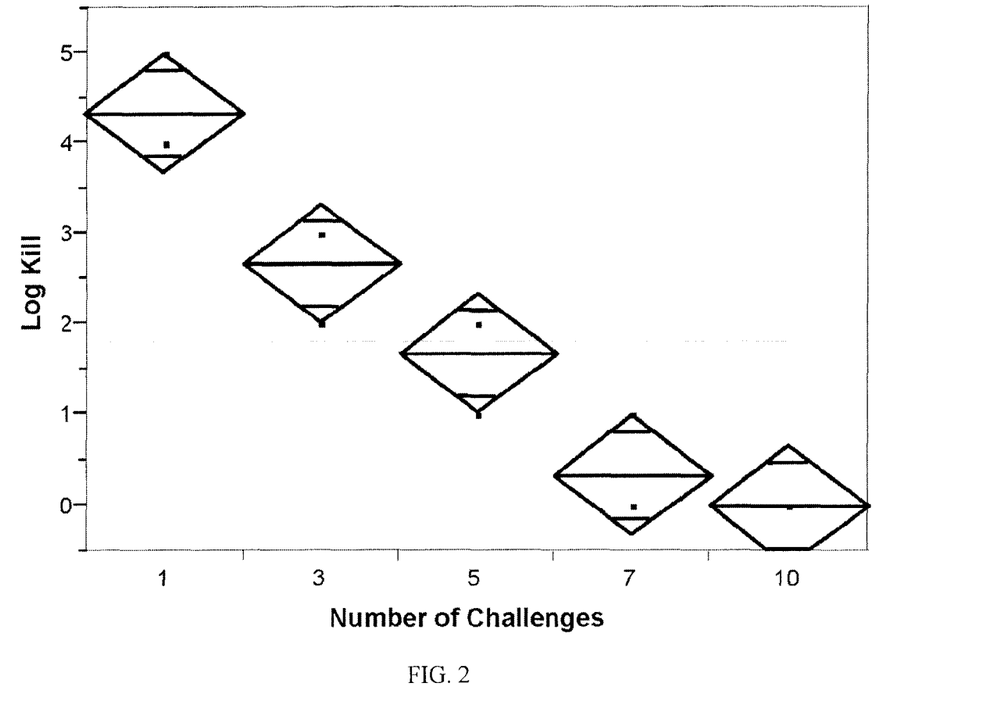
FIG. 2 is a graphical depiction of a 10× challenge of *Bacillus antthracis* (Sterne).

The SDS coatings demonstrate spore decontamination after five challenges by $10^7/cm^2$ *Bacillus anthracis* (Sterne). An average log kill of 2-3 was achieved at the third challenge.

TABLE 2

| Number of Challenges | Bacteria Challenge (CFU/ml) | Bacteria Recovered (CFU/ml) | Bacteria Reduction[1] (CFU/ml) | Log (Bacteria Reduction)[2] | Log Kill[3] |
|---|---|---|---|---|---|
| 1 | 1.E+07 | 1.E+02 | 1.E+05 | 5 | 5 |
| 1 | 1.E+07 | 1.E+03 | 1.E+04 | 4 | 4 |
| 1 | 1.E+07 | 1.E+03 | 1.E+04 | 4 | 4 |
| 3 | 1.E+07 | 1.E+04 | 1.E+03 | 3 | 3 |
| 3 | 1.E+07 | 1.E+04 | 1.E+03 | 3 | 3 |
| 3 | 1.E+07 | 1.E+04 | 1.E+03 | 2 | 2 |
| 5 | 1.E+07 | 1.E+05 | 1.E+02 | 2 | 2 |
| 5 | 1.E+07 | 1.E+06 | 1.E+01 | 1 | 1 |
| 5 | 1.E+07 | 1.E+05 | 1.E+02 | 2 | 2 |
| 7 | 1.E+07 | 1.E+06 | 1.E+01 | 1 | 1 |
| 7 | 1.E+07 | 1.E+07 | 0 | 0 | 0 |
| 7 | 1.E+07 | 1.E+07 | 0 | 0 | 0 |
| 10 | 1.E+07 | 1.E+07 | 0 | 0 | 0 |
| 10 | 1.E+07 | 1.E+07 | 0 | 0 | 0 |
| 10 | 1.E+07 | 1.E+07 | 0 | 0 | 0 |

[1] Bacteria Reduction = Bacteria Challenge − Bacteria Recovered
[2] Log (Bacteria Reduction) = Log (Bacteria Challenge) − Log (Bacteria Recovered)
[3] Log Kill = Log (Bacteria Reduction)$_{sample}$ − Log (Bacteria Reduction)$_{control}$; the control is a plain glass slide with a measured Log (Bacteria Reduction) of 0.

Example 5

10× Challenge of *Staphylococcus aureus*

Self-decontaminating surface (SDS) demonstration coatings were prepared for the 10× challenge against *Staphylococcus aureus*. The purpose of the 10× challenge is to demonstrate the durability of the SDS coating over multiple exposures to bacteria.

Coatings were prepared from the aqueous based two part urethane (some acetone added) containing the nutrients/germinants, SAP microspheres and a biocide. The resin was applied to 1"×3" glass slides. To achieve a superhydrophobic surface, silica was applied as the coating become tacky followed by treatment with a fluorosilane.

*Staphylococcus aureus* is applied to the slides by aerosolizing from a solution of $10^9$. This is done in a special hood with filters to collect any of the bacteria that may escape. The solution is sprayed at a slight angle but not 45° to avoid beading and rolling off the surface. To insure application of $10^7/cm^2$, a blank glass slide is sprayed and swabbed followed by serial dilution. After spraying, the slides are placed in a petri dish with sterile damp filter paper to prevent to dessication for two hours before additional challenge trials. At each challenge, slides are removed and a one $cm^2$ swabbed for serial dilution.

Figure 3:
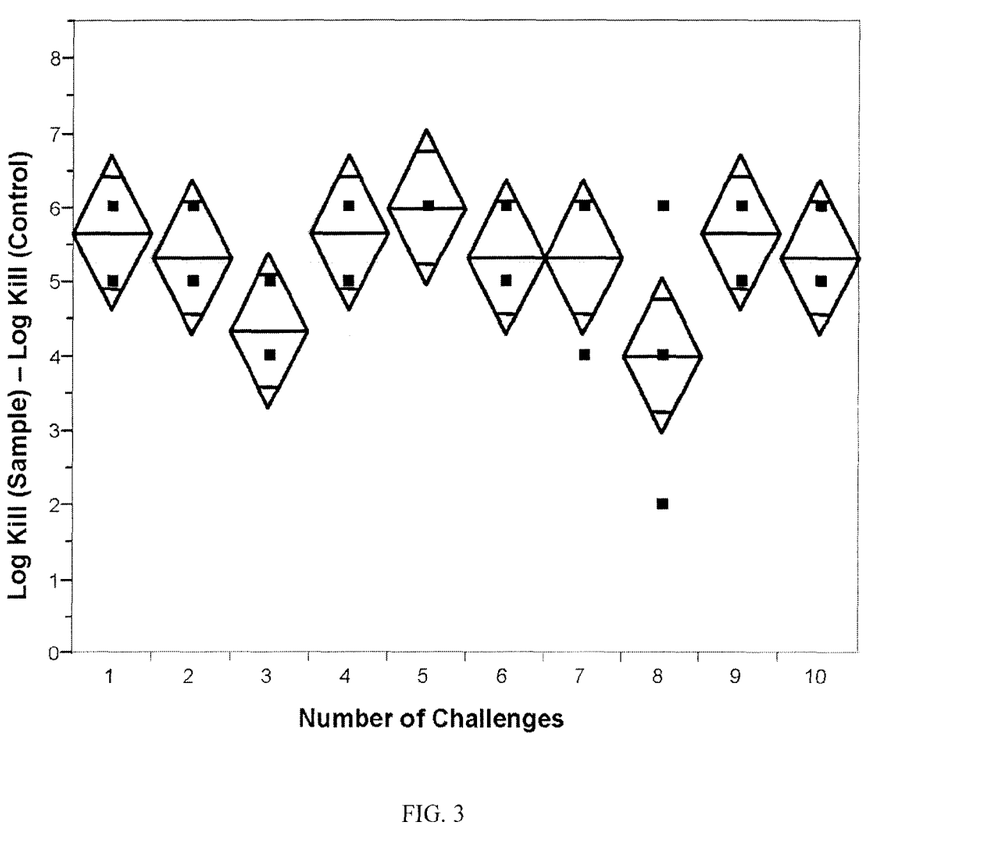
FIG. 3 is a graphical depiction of Log Kill exhibited by the SDS coating against *S. aureus* over 10 challenges of $10^7/cm^2$.

The data obtained from the 10× challenge is given in Table 3. The data is depicted graphically in FIG. 3. The data from each challenge is an average of three samples. The data is depicted in the graph as Mean Diamonds. The line across each diamond represents the group mean. The vertical span of each diamond represents the 95% confidence interval for each group. For groups with equal sample sizes, overlapping marks indicate that the two group means are not significantly different at the 95% confidence level.

TABLE 3

| Number of Challenges | Bacteria Challenge (CFU/ml) | Bacteria Recoved (CFU/ml) | Bacteria Reduction[1] (CFU/ml) | Log (Bacteria Reduction)[2] | Log Kill[3] |
|---|---|---|---|---|---|
| 1 | 1.E+07 | 0.E+00 | 1.E+07 | 7 | 6 |
| 1 | 1.E+07 | 0.E+00 | 1.E+07 | 7 | 6 |
| 1 | 1.E+07 | 1.E+01 | 1.E+06 | 6 | 5 |
| 2 | 1.E+07 | 1.E+01 | 1.E+06 | 6 | 5 |
| 2 | 1.E+07 | 1.E+01 | 1.E+06 | 6 | 5 |
| 2 | 1.E+07 | 0.E+00 | 1.E+07 | 7 | 6 |

TABLE 3-continued

| Number of Challenges | Bacteria Challenge (CFU/ml) | Bacteria Recoved (CFU/ml) | Bacteria Reduction[1] (CFU/ml) | Log (Bacteria Reduction)[2] | Log Kill[3] |
|---|---|---|---|---|---|
| 3 | 1.E+07 | 1.E+02 | 1.E+05 | 5 | 4 |
| 3 | 1.E+07 | 1.E+02 | 1.E+05 | 5 | 4 |
| 3 | 1.E+07 | 1.E+01 | 1.E+06 | 6 | 5 |
| 4 | 1.E+07 | 1.E+01 | 1.E+06 | 6 | 5 |
| 4 | 1.E+07 | 0.E+00 | 1.E+07 | 7 | 6 |
| 4 | 1.E+07 | 0.E+00 | 1.E+07 | 7 | 6 |
| 5 | 1.E+07 | 0.E+00 | 1.E+07 | 7 | 6 |
| 5 | 1.E+07 | 0.E+00 | 1.E+07 | 7 | 6 |
| 5 | 1.E+07 | 0.E+00 | 1.E+07 | 7 | 6 |
| 6 | 1.E+07 | 1.E+01 | 1.E+06 | 6 | 5 |
| 6 | 1.E+07 | 1.E+01 | 1.E+06 | 6 | 5 |
| 6 | 1.E+07 | 0.E+00 | 1.E+07 | 7 | 6 |
| 7 | 1.E+07 | 1.E+02 | 1.E+05 | 5 | 4 |
| 7 | 1.E+07 | 0.E+00 | 1.E+07 | 7 | 6 |
| 7 | 1.E+07 | 0.E+00 | 1.E+07 | 7 | 6 |
| 8 | 1.E+07 | 0.E+00 | 1.E+07 | 7 | 6 |
| 8 | 1.E+07 | 1.E+04 | 1.E+03 | 3 | 2 |
| 8 | 1.E+07 | 1.E+02 | 1.E+05 | 5 | 4 |
| 9 | 1.E+07 | 0.E+00 | 1.E+07 | 7 | 6 |
| 9 | 1.E+07 | 0.E+00 | 1.E+07 | 7 | 6 |
| 9 | 1.E+07 | 1.E+01 | 1.E+06 | 6 | 5 |
| 10 | 1.E+07 | 1.E+01 | 1.E+06 | 6 | 5 |
| 10 | 1.E+07 | 0.E+00 | 1.E+07 | 7 | 6 |
| 10 | 1.E+07 | 1.E+01 | 1.E+06 | 6 | 5 |

[1]Bacteria Reduction = Bacteria Challenge − Bacteria Recovered
[2]Log (Bacteria Reduction) = Log (Bacteria Challenge) − Log (Bacteria Recovered)
[3]Log Kill = Log (Bacteria Reduction)$_{sample}$ − Log (Bacteria Reduction)$_{control}$; the control is a plain glass slide with a measured Log (Bacteria Reduction) of 1.

The SDS coatings demonstrate a consistent high level of bacterial decontamination after ten challenges by $10^7/cm^2$ Staphylococcus aureus. An average log kill of 4-6 was achieved over the ten challenges. The SDS coating was just as effective at the tenth challenge as it was at the first challenge.

The above description and drawings are only illustrative of preferred embodiments which achieve the objects, features and advantages of the present invention, and it is not intended that the present invention be limited thereto.

What is claimed is:

1. A self-decontaminating surface coating comprising:
a cured hydrophilic polymeric coating resin;
a biocide in an effective amount for the purpose of killing microbial pathogens;
a superabsorbent polymer;
    wherein a germinating agent and a nutrient are absorbed into the superabsorbent polymer; and
hydrophobic particulates having dimensions of less than 100 micrometers protruding from the surface of the cured hydrophilic polymeric coating resin;
    wherein the self-decontaminating surface coating when cured has a partially hydrophobic three dimensional surface and is resistant to spores.

2. A self-decontaminating surface coating according to claim 1, wherein the cured hydrophilic polymeric coating resin has an equilibrium water uptake ranging from about 5% by weight to about 75% by weight of the cured resin.

3. A self-decontaminating surface coating according to claim 2, wherein the cured hydrophilic polymeric coating resin has an equilibrium water uptake of about 20% by weight of the cured resin.

4. A self-decontaminating surface coating according to claim 1, wherein the cured hydrophilic polymeric coating resin is selected from the group consisting of: a polyurethane; an epoxy; and an acrylic.

5. A self-decontaminating surface coating according to claim 4, wherein the cured hydrophilic polymeric coating resin is selected from the group consisting of: a cationic water dispersed polyurethane and a hydrophilic isophorone diisocyanate prepolymer.

6. A self-decontaminating surface coating according to claim 1, wherein the biocide is selected from the group consisting of: phenols; substituted phenols; hypochlorites; formaldehydes; gluteraldehydes; mecurials; quaternary ammonium compounds; pyridinium compounds; aliphatic alcohols; amines; sulfates; carboxylic acids; ethanols; peperdine-N-oxide; chlorohexidines; azideisothiazolones; iodoacetates; heavy metal salts; chloroacetamides; oxines; peroxide releasing agents; peracetic acids; aminoacrilines; and chlorophenols.

7. A self-decontaminating surface coating according to claim 1, wherein the biocide ranges from about 0.05% by weight to about 5% by weight of the cured coating.

8. A self-decontaminating surface coating according to claim 1, wherein the germinating agent is selected from the group consisting of: L-alanine and L-methionine.

9. A self-decontaminating surface coating according to claim 1, wherein the germinating agent ranges from about 0.1% by weight to about 5% by weight of the cured coating.

10. A self-decontaminating surface coating according to claim 9, wherein the germinating agent comprises about 1% by weight of the cured coating.

11. A self-decontaminating surface coating according to claim 1, wherein the nutrient is selected from the group consisting of: Luria broth; yeast extract;

; and

12. A self-decontaminating surface coating according to claim 11, wherein the nutrient comprises up to about 5% by weight of the cured coating.

13. A self-decontaminating surface coating according to claim 12, wherein the nutrient comprises about 1% by weight of the cured coating.

14. A self-decontaminating surface coating according to claim 1, wherein the superabsorbant polymer is selected from the group consisting of: hydrolysis products of starch acrylonitrile graft polymers; carboxymethylcellulose; crosslinked polyacrylates; sulfonated polystyrenes; polyacrylamides; polyvinyl alcohols; polyethylene oxides; polyvinylpyrrolidones; and polyacrylonitriles.

15. A self-decontaminating surface coating according to claim 1, wherein the superabsorbant polymer is in the form of a particulate having a mesh size ranging from about 1 micron to about 200 microns.

16. A self-decontaminating surface coating according to claim 15, wherein the superabsorbant polymer is in the form of a particulate having a mesh size ranging from about 5 microns to about 50 microns.

17. A self-decontaminating surface coating according to claim 1, wherein the coating has an advancing contact angle greater than 150 degrees and a receding water contact angle greater than 150 degrees when the coating is fully cured.

18. A method for preparing an article having a self-decontaminating surface, the method comprising the steps of:
   a) providing an article;
   b) applying to the article a composition comprising:
      a polymeric coating resin wherein the polymeric coating resin is hydrophilic when cured;
      a biocide in an effective amount for the purpose of killing microbial pathogens;
      a superabsorbent polymer;
      wherein a germinating agent and a nutrient are absorbed into the superabsorbent polymer;
   c) curing the self-decontaminating surface coating on the article to have a tacky surface; and
   d) sprinkling hydrophobic particulates having dimensions of less than 100 micrometers on the tacky surface.

19. The article prepared by the method according to claim 18.

20. An article having a self-decontaminating surface, wherein the article comprises the self-decontaminating surface coating according to claim 1 disposed on at least one surface of the article.

21. A self-decontaminating surface coating according to claim 1, wherein the hydrophobic particulates comprise silica treated with fluorosilane.

* * * * *